United States Patent [19]

Budz et al.

[11] Patent Number: 5,418,127
[45] Date of Patent: May 23, 1995

[54] WATER-SOLUBLE DISULFIDES IN SILVER HALIDE EMULSIONS

[75] Inventors: Jerzy A. Budz, Fairport; George J. Burgmaier, Pittsford; Roger L. Klaus; Xin Wen, both of Rochester, all of N.Y.

[73] Assignee: Eastman Kodak Company, Rochester, N.Y.

[21] Appl. No.: 210,826

[22] Filed: Mar. 18, 1994

Related U.S. Application Data

[63] Continuation-in-part of Ser. No. 68,814, May 28, 1993, abandoned.

[51] Int. Cl.[6] .......................... G03C 1/34; G03C 1/09
[52] U.S. Cl. ..................................... 430/611; 430/567
[58] Field of Search .............................. 430/611, 567

[56] References Cited

U.S. PATENT DOCUMENTS

| | | |
|---|---|---|
| 2,948,614 | 8/1960 | Allen et al. . |
| 3,043,696 | 7/1962 | Herz et al. . |
| 3,057,725 | 10/1962 | Herz et al. . |
| 3,062,654 | 11/1962 | Allen et al. . |
| 3,128,186 | 4/1964 | Corben et al. . |
| 3,226,232 | 12/1965 | Dersch et al. . |
| 3,297,713 | 1/1967 | Ladd ................... 260/326.3 |
| 3,318,701 | 5/1967 | Corben . |
| 3,397,986 | 8/1968 | Millikan et al. . |
| 3,409,437 | 11/1968 | Copeland et al. . |
| 3,447,925 | 6/1969 | Dersch et al. . |
| 3,597,207 | 9/1971 | Kuh et al. . |
| 3,672,902 | 6/1972 | van Stappen et al. . |
| 3,761,277 | 9/1973 | Vandenberghe et al. . |
| 3,779,757 | 12/1973 | Hofman et al. . |
| 3,926,632 | 12/1975 | Hofman et al. . |
| 4,521,508 | 6/1985 | Sugimoto et al. . |
| 4,699,873 | 10/1987 | Takahashi et al. . |
| 4,920,043 | 4/1990 | Ohashi et al. . |
| 4,923,793 | 5/1990 | Shibahara . |
| 5,217,859 | 6/1993 | Boettcher et al. . |

FOREIGN PATENT DOCUMENTS

| | | |
|---|---|---|
| 0080451 | 6/1983 | European Pat. Off. . |
| 0454149 | 10/1991 | European Pat. Off. . |
| 0617320 | 9/1994 | European Pat. Off. . |
| 1472883 | 1/1969 | Germany . |
| 2244916 | 9/1971 | Germany . |
| 62/58240 | 3/1987 | Japan . |
| 63/50833 | 3/1988 | Japan . |
| 105236 | 4/1989 | Japan . |
| 3071131 | 3/1991 | Japan . |

OTHER PUBLICATIONS

Farmaco, Edizione Scientifica, vol. 24, No. 2, Feb. 1970, Pacia It, pp. 106–111.
Research Disclosure 29658, Dec. 1988, pp. 976–978, Disclosed by Piet Kok et al. of Agfa-Gevaert N.V.
CA 116(6):48968n, PY 1991.
RN 26461-53-0 Registry, 8CI, 1967.

*Primary Examiner*—Thorl Chea
*Attorney, Agent, or Firm*—Peter C. Cody

[57] ABSTRACT

A disulfide compound represented by the following formula:

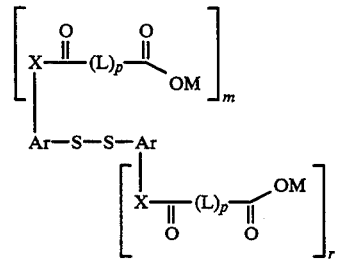

wherein
X is independently —O—, —NH— or —NR—, where R is a substituent;
m and r are independently 0, 1 or 2;
M is —H or a cationic species;
Ar is an aromatic group; and
L is a linking group, where p is 0 or 1.

A silver halide emulsion comprising said disulfide compounds and a photographic element comprising a silver halide emulsion in reactive association with said disulfide compounds and a method of making same.

17 Claims, No Drawings

WATER-SOLUBLE DISULFIDES IN SILVER HALIDE EMULSIONS

CROSS-REFERENCE TO RELATED APPLICATIONS

This is a continuation-in-part of application Ser. No. 08/068,814, filed May 28, 1993, now abandoned.

FIELD OF THE INVENTION

The present invention relates to new water-soluble disulfide compounds and their use in light-sensitive silver halide emulsions.

BACKGROUND OF THE INVENTION

Problems with fogging have plagued the photographic industry from its inception. Fog is a deposit of silver or dye that is not directly related to the image-forming exposure, i.e., when a developer acts upon an emulsion layer, some reduced silver is formed in areas that have not been exposed to light. Fog can be defined as a developed density that is not associated with the action of the image-forming exposure, and is usually expressed as "D-min", the density obtained in the unexposed portions of the emulsion. Density, as normally measured, includes both that produced by fog and that produced as a function of exposure to light. It is known in the art that the appearance of photographic fog related to intentional or unintentional reduction of silver ion (reduction sensitization) can occur during many stages of preparation of the photographic element including silver halide emulsion preparation, spectral/chemical sensitization of the silver halide emulsion, melting and holding of the liquid silver halide emulsion melts, subsequent coating of silver halide emulsions, and prolonged natural and artificial aging of coated silver halide emulsions.

The control of fog, whether occurring during the formation of the light-sensitive silver halide emulsion, during the spectral/chemical sensitization of those emulsions, during the preparation of silver halide compositions prior to coating on an appropriate support, or during the aging of such coated silver halide compositions, has been attempted by a variety of means. Mercury-containing compounds, such as those described in U.S. Pat. Nos. 2,728,663; 2,728,664; and 2,728,665, have been used as additives to control fog. Thiosulfonates and thiosulfonate esters, such as those described in U.S. Pat. Nos. 2,440,206; 2,934,198; 3,047,393; and 4,960,689, have also been employed. Organic dichalcogenides, for examples the disulfide compounds described in U.S. Pat. Nos. 1,962,133; 2,465,149; 2,756,145; 2,935,404; 3,184,313; 3,318,701; 3,409,437; 3,447,925; 4,243,748; 4,463,082; and 4,788,132 have been used not only to prevent formation of fog but also as desensitizers and as agents in processing baths and as additives in diffusion transfer systems.

Unfortunately, such fog reducing compounds are not without drawbacks. Mercury-containing compounds at relatively low concentrations can diminish the sensitivity of silver halide emulsions, can cause a deterioration in the stability of the latent image, and are environmentally harmful. The elimination of mercury-containing compounds from photographic compositions is highly desirable. Thiosulfonate salts can cause large sensitivity losses if not used with an excess of sulfinate salt. Many of the very effective organic disulfide compounds need to be added to silver halide compositions from typical organic solvents because of their high water insolubility. This has several drawbacks, for example, coagulation of hydrophilic binders by the solvents, rapid flocculation and crystallization of the disulfide compounds when added to aqueous melts, solvent explosion hazards, and the potential for environmentally harmful solvent emissions.

One method used to overcome some of the problems associated with organic disulfide compounds is to prepare a solid particle dispersion, such as described in U.S. patent application Ser. No. 07/869,678, Boettcher et al., filed Apr. 16, 1992. However, this method, while effective, requires the additional steps and costs of dispersion preparation, certification, and handling. Further, the use of gelatin-containing dispersions has limitations when the presence of gelatin is undesired, such as during the precipitation of silver halide emulsions in synthetic protective colloids.

Some water-soluble disulfide compounds have been described for use with photographic elements. U.S. Pat. Nos. 3,057,725 and 3,062,654 describe substituted alkylene disulfides as antifoggants in silver halide emulsions. U.S. Pat. No. 3,226,232 describes the free acids of carboxyphenyl disulfides as antifoggants and stabilizers in silver halide emulsions. U.S. Pat. No. 3,597,207 discusses bis(loweralkylcarbonamidophenyl) disulfides for use in pretreatment solutions for processing color reversal compositions. U.S. Pat. No. 3,761,277 discusses sulfophenyl-substituted disulfides as fog stabilizers. U.S. Pat. No. 3,779,757 describes aromatic acid-substituted disulfides for diffusion transfer as image toners. U.S. Pat. No. 3,926,632 broadly describes a class of disulfides which are utilized solely in fine-grained lith materials. U.S. Pat. No. 4,521,508 describes aromatic or heterocyclic disulfides as additives in internally fogged silver halide emulsions. U.S. Pat. No. 4,699,873 describes the disulfides of U.S. Pat. No. 4,521,508 in combination with hydrazines in high-chloride-content graphic arts material.

None of the disulfide compounds known in the art, however, have the combined attributes of high water solubility and strong antifogging activity with de minimus impact on sensitivity. A photographic additive with these qualities is highly desired in the photographic industry.

SUMMARY OF THE INVENTION

This invention provides a disulfide compound represented by the following formula:

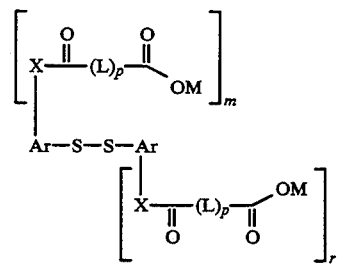

wherein

X is independently —O—, —NH— or —NR—, where R is a substituent;

m and r are independently 0, 1 or 2;

M is —H or a cationic species;

Ar is an aromatic group; and

L is a linking group, where p is 0 or 1.

This invention further provides a silver halide emulsion comprising said disulfide compounds and a photographic element comprising a silver halide emulsion in reactive association with said disulfide compounds. This invention also provides a method of making a silver halide emulsion comprising adding to the emulsion said disulfide compounds and a silver halide emulsion prepared by this method.

Also provided by this invention is a silver halide photographic element comprising a silver halide emulsion and a compound represented by the following formula:

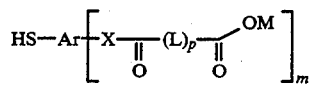

wherein
X is independently —O—, —NH— or —NR—, where R is a substituent;
m is 1 or 2;
M is —H— or a cationic species;
Ar is an aromatic group; and
L is a linking group, where p is 0 or 1.

The disulfide compounds of this invention are surprisingly effective at reducing the exposure sensitivity of silver chloride emulsions to heat. They are also highly effective at stabilizing, without greatly affecting sensitivity, coated silver halide emulsions against speed and fog changes after storage. The disulfide compounds of this invention are also useful as crystal growth modifiers. These disulfide compounds may be easily prepared from common reagents.

The disulfide compounds of this invention are water soluble; therefore, their use in silver halide emulsions and photographic elements alleviates the need for volatile organic solvents and circumvents the disadvantages of using solid particle dispersions. In addition, the use of these disulfide compounds eliminates the need for mercury-containing compounds, an environmentally desirable goal.

DETAILED DESCRIPTION OF THE INVENTION

The disulfide compounds of this invention are represented by following formula:

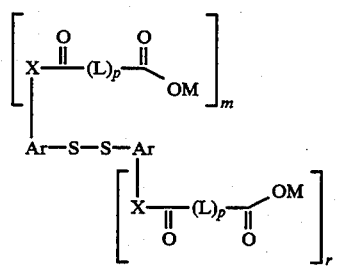

Ar is an aromatic group either of a single ring or a condensed ring, preferably having 6 to 10 carbon atoms and more preferably having 6 carbon atoms. Examples of suitable aromatic groups include naphthyl and phenyl. Ar may be further substituted or may be unsubstituted, more preferably Ar is unsubstituted. Examples of suitable substituents include alkyl groups (for example, methyl, ethyl, hexyl), fluoroalkyl groups (for example, trifluoromethyl), alkoxy groups (for example, methoxy, ethoxy, octyloxy), aryl groups (for example, phenyl, naphthyl, tolyl), hydroxyl groups, halogen atoms, aryloxy groups (for example, phenoxyl), alkylthio groups (for example, methylthio, butylthio), arylthio groups (for example, phenylthio), acyl groups (for example, acetyl, propionyl, butyryl, valeryl), sulfonyl groups (for example, methylsulfonyl, phenylsulfonyl), acylamino groups, sulfonylamino groups, acyloxy groups (for example, acetoxy, benzoxy), carboxyl groups, cyano groups, sulfo groups, and amino groups. Preferred are simple alkyl groups and acylamino groups.

X is independently an —O—, —NH— or —NR—. Most preferably X is —NH—. If X is —NR—, R is a substituent which does not interfere with the intended function of the disulfide compound in the photographic emulsion and which maintains the water solubility of the compound. Examples of suitable substituents include alkyl groups (for example, methyl, ethyl, hexyl), fluoroalkyl groups (for example, trifluoromethyl), aryl groups (for example, phenyl, naphthyl, tolyl), sulfonyl groups (for example, methylsulfonyl, phenylsulfonyl). Preferred are simple alkyl groups and simple fluoroalkyl groups.

r and m are independently 0, 1 or 2. Therefore, included are those compounds in which only one of the aromatic groups is substituted. Preferably m and r are both 1. X is independently in any position in the aromatic nucleus relative to the sulfur. More preferably, the molecule is symmetrical and preferably X is either in the para or ortho position.

L is a linking group. p is 0 or 1. Preferably L is a unsubstituted alkylene group and is usually —(CH$_2$)$_n$— where n ranges from zero to 11 and is preferably 1 to 3. Other examples of L are given below,

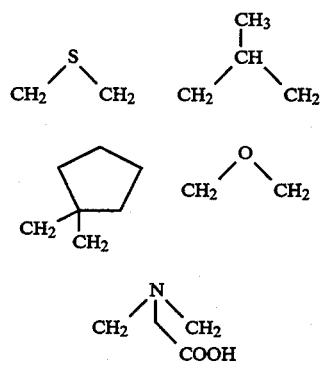

M is either a hydrogen atom or a cationic species if the carboxyl group is in its ionized form. The cationic species may be a metal ion or an organic ion. Examples of organic cations include ammonium ions (for example, ammonium, tetramethylammonium, tetrabutylammonium), phosphonium ions (for example, tetraphenylphosphonium), and guanidyl groups. Preferably M is hydrogen or an alkali metal cation, with a sodium or potassium ion being most preferred.

Examples of the disulfide compounds of this invention are shown below. Compounds I-A through I-H are preferred with Compounds I-D and I-E being most preferred.

-continued

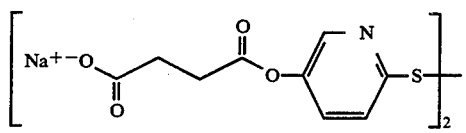  I-R

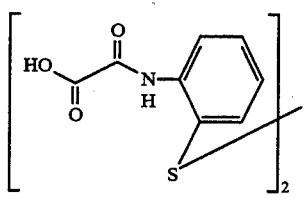  I-S

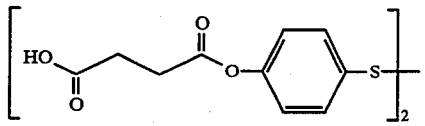  I-T

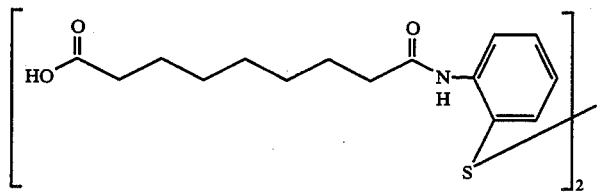  I-U

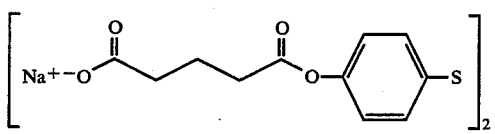  I-V

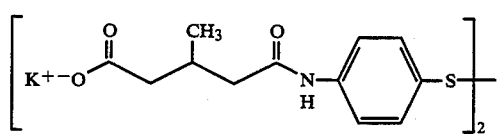  I-W

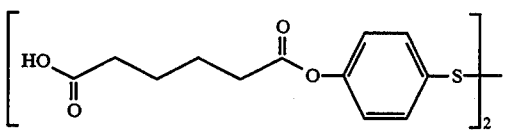  I-X

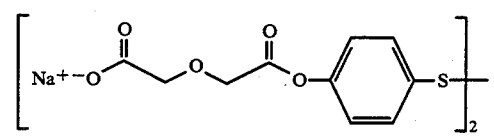  I-Y

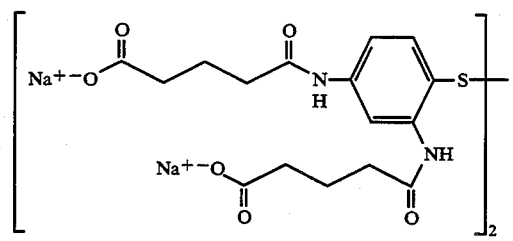  I-Z

The solubilized disulfides of this invention are easily prepared using readily available starting materials. Most of the solubilized disulfides can be obtained by reacting aminophenyl disulfide or hydroxyphenyl disulfide with the appropriate cyclic anhydride followed by conversion of the free diacid to its anionic form using materials such as sodium bicarbonate. Other solubilized disulfides could be obtained by reacting aminophenyl disulfide or hydroxyphenyl disulfide with the mono chloride of a dicarboxylic acid mono ester, followed by hydrolysis of the ester to the carboxylic acid.

The photographic emulsions of this invention are generally prepared by precipitating silver halide crystals in a colloidal matrix by methods conventional in the art. The colloid is typically a hydrophilic film forming agent such as gelatin, alginic acid, or derivatives thereof.

The crystals formed in the precipitation step are chemically and spectrally sensitized, as known in the art. Chemical sensitization of the emulsion employs sensitizers such as sulfur-containing compounds, e.g., allyl isothiocyanate, sodium thiosulfate and allyl thiourea; reducing agents, e.g., polyamines and stannous salts; noble metal compounds, e.g., gold, platinum; and polymeric agents, e.g., polyalkylene oxides. A temperature rise is employed to complete chemical sensitization (heat treatment). Spectral sensitization is effected with agents such as sensitizing dyes. For color emulsions, dyes are added in the spectral sensitization step using any of a multitude of agents described in the art. It is known to add such dyes both before and after heat treatment.

After spectral sensitization, the emulsion is coated on a support. Various coating techniques include dip coating, air knife coating, curtain coating and extrusion coating.

The disulfide compounds of this invention may be added to the silver halide emulsion at any time during the preparation of the emulsion, i.e., during precipitation, during or before chemical sensitization or during final melting and co-mixing of the emulsion and additives for coating. The greatest overall antifogging activity with the least reduction in sensitivity is seen if the disulfide compound is added after precipitation and before or during chemical sensitization.

The disulfide compounds may be added to any layer where they are in reactive association with the silver halide. By "in reactive association with" it is meant that the disulfide compounds must be contained in the silver halide emulsion layer or in a layer whereby they can react or interreact with the silver halide emulsion. For example, they can also be added to gelatin-only overcoats or interlayers, or to water-only overcoats.

In one embodiment the disulfide compounds may react with the silver halide emulsion to form mercapto compounds of the formula

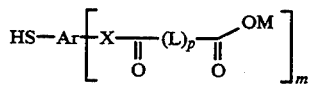

wherein
X is independently —O—, —NH—, or —NR—, where R is a substituent;
m is 1 or 2;
M is —H or a cationic species;
Ar is an aromatic group; and
L is a linking group where p is 0 or 1.

X, R, M, Ar and L are the same as described above for the disulphide compounds. Such mercapto compounds may be present in the photographic element, particularly when the disulfide compounds of this invention are added during an early stage of the emulsion making process.

When the disulfide compounds of this invention are added prior to or during precipitation, they can be added to the vessel containing the aqueous gelatin salt solution before the start of the precipitation; they can also be added during precipitation to the salt solution, the silver nitrate solution, or from a separate jet directly into the kettle. However, there is some indication that greater activity may be achieved if the disulfides are added in the salt solution or directly to the vessel before the start of precipitation. The compounds can be added from the beginning or part-way-through precipitation. Parameters such as temperature, stirring time and other variables for precipitating conventional emulsions are known to those skilled in the art. When added before or during precipitation the disulfides of this invention can be utilized as antifoggants or as crystal growth modifiers such as described in U.S. patent application Ser. No. 07/869,670, of Kim et al., filed Apr. 16, 1992.

When the disulfide compounds are added from an aqueous solution it is advantageous to use the alkaline earth salt of the disulfide. Alternatively, the free acid can be used by co-dissolution with appropriate molar equivalents of base, or the free acid can be prepared as a solid particle dispersion and added to the silver halide emulsion, gelatin-only overcoat, or interlayer. Preferably the disulfide compounds are added as the aqueous solution of the alkaline earth salt. Additionally, the disulfide compounds of this invention can be used in combination with sulfinate salts as described in U.S. patent application Ser. No. 978,539, Klaus and Leonard, filed Nov. 19, 1993.

The optimal amount of the disulfide compound to be added will depend on the desired final result, the type of emulsion, the degree of ripening, the point of addition, the chemical structure, and other variables. In general the concentration of disulfide compound which may be utilized is from about $1 \times 10^{-9}$ to about $1 \times 10^{-2}$ mol/mol Ag, with $1 \times 10^{-7}$ to $1 \times 10^{-2}$ mol/mol Ag being preferred and about $1 \times 10^{-5}$ to $8 \times 10^{-4}$ mol/mol Ag being most preferred. The more preferred range for the growth modification properties is $1 \times 10^{-5}$ to $1 \times 10^{-3}$ mol/mol Ag.

Combinations of the disulfide compounds of this invention may be used. The disulfide compounds also may also be used in combination with other antifoggants and finish modifiers.

The disulfide compounds of this invention may be utilized with any type of silver halide emulsion, for example silver bromide, silver iodobromide, silver iodochlorobromide, silver chlorobromide, and silver chloride. Surprisingly, however, it has been discovered that the disulfide compounds provide excellent heat stability in high chloride emulsions. Therefore, in one embodiment of the invention it is preferred that the silver halide emulsion contain at least 50 mole % silver chloride, and more preferably 90 mole % silver chloride.

The disulfide compounds of this invention are particularly useful with intentionally or unintentionally reduction sensitized emulsions. As described in *The Theory of the Photographic Process*, 4th edition, T. H. James, Macmillan Publishing Company, Inc., 1977, pages 151-152, reduction sensitization has been known to improve the photographic sensitivity of silver halide emulsions. Reduction sensitization can be performed intentionally by adding reduction sensitizers, chemicals which reduce silver ions to form metallic silver atoms, or by providing a reducing environment such as high pH (excess hydroxide ion) and/or low pAg (excess silver ion).

During precipitation of a silver halide emulsion, unintentional reduction sensitization can occur when silver nitrate or alkali solutions are added rapidly or with poor mixing to form emulsion grains, for example. Also silver halide emulsions precipitated in the presence of ripeners (grain growth modifiers) such as thioethers, selenoethers, thioureas, or ammonia tend to facilitate reduction sensitization.

Examples of reduction sensitizers and environments which may be used during precipitation or spectrochemical sensitization to reduction sensitize an emulsion include ascorbic acid derivatives; tin compounds; polyamine compounds; and thiourea dioxide-based compounds described in U.S. Pat. Nos. 2,487,850; 2,512,925; and British Patent 789,823. Specific examples of reduction sensitizers or conditions, such as dimethylaminoborane, stannous chloride, hydrazine, high pH (pH 8-11) and low pAg (pAg 1-7) ripening are discussed by S. Collier in Photographic Science and Engineering, 23,113 (1979).

Examples of processes for preparing intentionally reduction sensitized silver halide emulsions are described in EP 0 348934 A1 (Yamashita), EP 0 369491 (Yamashita), EP 0 371388 (Ohashi,), EP 0 396424 A1 (Takada), EP 0 404142 A1 (Yamada) and EP 0 435355 A1 (Makino).

The disulfide compounds of this invention are also particularly useful with emulsions doped with Group VIII metals such as iridium, rhodium, osmium and iron as described in *Research Disclosure*, December 1989, Item 308119, published by Kenneth Mason Publications, Ltd., Dudley Annex, 12a North Street, Emswirth, Hampshire P010 7DQ, ENGLAND. It is common practice in the art to dope emulsions with these metals for reciprocity control.

A general summary of the use of iridium in the sensitization of silver halide emulsions is contained in Carroll, "Iridium Sensitization: A Literature Review," Photographic Science and Engineering, Vol. 24, No. 6, 1980.

A method of manufacturing a silver halide emulsion by chemically sensitizing the emulsion in the presence of an iridium salt and a photographic spectral sensitizing dye is described in U.S. Pat. No. 4,693,965. The low intensity reciprocity failure characteristics of a silver halide emulsion may be improved, without significant reduction of high intensity speed, by incorporating iridium ion into the silver halide grains after or toward the end of the precipitation of the grains is described in U.S. Pat. No. 4,997,751. The use of osmium in precipitating an emulsion is described in U.S. Pat. No. 4,933,272 (McDugle).

In some cases, when such dopants are incorporated, emulsions show increased fresh fog and a lower contrast sensitometric curve when processed in the color reversal E-6 process as described in The British Journal of Photography Annual, 1982, pages 201–203.

The photographic elements of this invention can be non-chromogenic silver image forming elements. They can be single color elements or multicolor elements. Multicolor elements typically contain dye image-forming units sensitive to each of the three primary regions of the visible spectrum. Each unit can be comprised of a single emulsion layer or of multiple emulsion layers sensitive to a given region of the spectrum. The layers of the element, including the layers of the image-forming units, can be arranged in various orders as known in the art. In an alternative format, the emulsions sensitive to each of the three primary regions of the spectrum can be disposed as a single segmented layer, e.g., as by the use of microvessels as described in Whitmore U.S. Pat. No. 4,362,806 issued Dec. 7, 1982. The element can contain additional layers such as filter layers, interlayers, overcoat layers, subbing layers and the like. This invention may be particularly useful with those photographic elements containing a magnetic backing such as described in No. 34390, *Research Disclosure*, November, 1992.

In the following discussion of suitable materials for use in the emulsions and elements of this invention, reference will be made to *Research Disclosure*, December 1989, Item 308119, published by Kenneth Mason Publications, Ltd., Dudley Annex, 12a North Street, Emsworth, Hampshire P010 7DQ, ENGLAND, the disclosures of which are incorporated herein by reference. This publication will be identified hereafter by the term "Research Disclosure"

The silver halide emulsions employed in the elements of this invention can be either negative-working or positive-working. Examples of suitable emulsions and their preparation are described in Research Disclosure Sections I and II and the publications cited therein. Other suitable emulsions are (111) tabular silver chloride emulsions such as described in U.S. Pat. Nos. 5,176,991 (Jones et al); 5,176,992 (Maskasky et al); 5,178,997 (Maskasky); 5,178,998 (Maskasky et al); 5,183,732 (Maskasky); and 5,185,239 (Maskasky) and (100) tabular silver chloride emulsions such as described in EPO 534,395, published Mar. 31, 1993 (Brust et al). Some of the suitable vehicles for the emulsion layers and other layers of elements of this invention are described in Research Disclosure Section IX and the publications cited therein.

The silver halide emulsions can be chemically and spectrally sensitized in a variety of ways, examples of which are described in Sections III and IV of the Research Disclosure. The elements of this invention can include various dye-forming couplers including but not limited to those described in Research Disclosure Section VII, paragraphs D, E, F and G and the publications cited therein. These couplers can be incorporated in the elements and emulsions as described in Research Disclosure Section VII, paragraph C and the publications cited therein.

The photographic elements of this invention or individual layers thereof can contain, among other things, brighteners (Examples in Research Disclosure Section V), antifoggants and stabilizers (Examples in Research Disclosure Section VI), antistain agents and image dye stabilizers (Examples in Research Disclosure Section VII, paragraphs I and J), light absorbing and scattering materials (Examples in Research Disclosure Section VIII), hardeners (Examples in Research Disclosure Section X), plasticizers and lubricants (Examples in Research Disclosure Section XII), antistatic agents (Examples in Research Disclosure Section XIII), matting agents (Examples in Research Disclosure Section XVI) and development modifiers (Examples in Research Disclosure Section XXI).

The photographic elements can be coated on a variety of supports including but not limited to those described in Research Disclosure Section XVII and the references described therein.

Photographic elements can be exposed to actinic radiation, typically in the visible region of the spectrum, to form a latent image as described in Research Disclosure Section XVIII and then processed to form a visible dye image examples of which are described in Research Disclosure Section XIX. Processing to form a visible dye image includes the step of contacting the element with a color developing agent to reduce developable silver halide and oxidize the color developing agent. Oxidized color developing agent in turn reacts with the coupler to yield a dye.

With negative working silver halide, the processing step described above gives a negative image. To obtain a positive (or reversal) image, this step can be preceded by development with a non-chromogenic developing agent to develop exposed silver halide, but not form dye, and then uniformly fogging the element to render unexposed silver halide developable, and then developed with a color developer. Additionally, the preceding process can be employed but before uniformly fogging the emulsion the remaining silver halide is dissolved and the developed silver is converted back to silver halide; the conventional E-6 process is then continued and results in a negative color image. Alternatively, a direct positive emulsion can be employed to obtain a positive image.

Development is followed by the conventional steps of bleaching, fixing, or bleach-fixing, to remove silver and silver halide, washing and drying.

The following examples are intended to illustrate, without limiting, this invention.

EXAMPLES

These compounds are utilized in the following examples.

Compound A=Thiourea dioxide
Compound B=Sodium thiosulfate pentahydrate
Compound C=Potassium tetrachloroaurate
Compound D=Bis(p-acetamidophenyl)disulfide
Compound E=Bis(2-amino-5-iodopyridine-dihydroiodide)mercuric iodide Compound F = Glycerin
Compound G = Saponin
Compound H = Bis(vinylsulfonylmethyl)ether
Compound I-A = Bis(potassium p-oxalamidophenyl)disulfide
Compound I-B = Bis(sodium p-oxalamidophenyl)disulfide
Compound I-C = Bis(sodium p-succinamidophenyl)disulfide
Compound I-D = Bis(sodium o-succinamidophenyl)disulfide
Compound I-E = Bis(sodium p-glutaramidophenyl)disulfide
Compound I-H = Bis(sodium o-glutaramidophenyl)disulfide
Compound J = Mercuric chloride
Compound K = Sodium thiocyanate
Compound L = Sodium aurous (I) dithiosulfate dihydrate
Compound M = Anhydro-9-ethyl-5,5'-dichloro-3,3'-bis-(2-hydroxy-3-sulfopropyl)thiacarbocyanine hydroxide sodium salt
Compound N = Anhydro-9-ethyl-5,5'-dimethyl(-3,3'-di(3-disulfopropyl)thiacarbocyanine hydroxide triethylamine salt
Compound O = Hexanamide,2-[2,4-bis(1,1-dimethylpropyl)phenoxy]-N-[4-[(2,2,3,3,4,4,4-heptafluoro-1-oxobutyl)amino]-3-hydroxyphenyl]
Compound P = 4-hydroxy-6-methyl-1,3,3a,7-tetraazaindene sodium salt
Compound Q = 5-thioctic acid
Compound R = Bis(o-carboxyphenyl)disulfide
Compound S = N-methylsulfamoylethyl benzothiazolium tetrafluoroborate

EXAMPLE 1

To a five-liter three-necked flask equipped with a mechanical stirrer, reflux condenser and drying tube was added a solution of 302.78 g p-aminophenyl disulfide dissolved in 1500 mL dry tetrahydrofuran (THF) (4A molecular sieves) followed by a solution of 299.05 g glutaric anhydride in 1800 mL dry THF. The solution was heated to 40° C. at which time an exotherm occurred. The reaction mixture was heated at reflux for an additional 30 min and then for an additional 75 min without auxiliary heating. The solid which had crystallized was collected from the still-warm suspension, washing with more THF, obtaining 531.4 g white solid, mp 225–7° C. To a 12-liter round-bottom flask equipped with a mechanical stirrer was added 525.00 g of the diacid and 184.82 g (2.20 mole) sodium bicarbonate followed by 850 mL water. The paste was heated slowly with steam heat until the evolution of carbon dioxide ceased. The nearly complete solution was filtered to remove trace insoluble materials, and the warm, pale-yellow filtrate was diluted with 6 L hot ethanol. The solid which formed was collected, obtaining 491.1 g white powder.

EXAMPLE 2

To a solution of 47.42 g p-aminophenyl disulfide in 750 mL dry THF was added 58 mL triethyl amine followed by the dropwise addition of a solution of 53.69 g ethyl oxalyl chloride in 50 mL dry THF. The addition, which was complete in 5 minutes, was accompanied by an exotherm to 55° C. After stirring at ambient temperature for an additional one hr the solid which had formed was removed by filtration, and the filtrate concentrated and poured into 3 L water containing 25 mL concentrated HCl. The solid which formed was collected and dried obtaining 84.92 g product, mp 158.0°–158.5° C. The diester was converted to the dicarboxylic acid by adding 28.0 g of the diester to a mixture of 200 mL acetic acid and 20 mL concentrated hydrochloric acid and heating at 70° C. for 2 hr. The solid which crystallized from the reaction mixture upon cooling to 20° C. was collected and recrystallized from 200 mL methanol, obtaining 9.84 g white solid.

EXAMPLE 3

Five-mL portions of water were added to separate test tubes at room temperature. All compounds were added separately to the individual test tubes until the solutions were saturated. For free acids, dissolution was aided by co-additions of sodium bicarbonate as described in Shriner et al, "The Systematic Identification of Organic Compounds", sixth edition, Wiley, N.Y., pp. 90–108. If the remaining solid dissolved, more was added until saturated. The tubes were covered and placed in hot water for 30 minutes and then allowed to cool to room temperature. Four mL of each clear solution was separated from the residual solids and placed into pre-weighed 25-mL flasks and allowed to evaporate under vacuum. The difference in weight between the flasks with and without residual solids gave a measure of maximum solubility in water at room temperature.

TABLE I

| Disulfide | | Maximum Solubility, RT g/L |
|---|---|---|
| Compound D | comparison, U.S. Pat. No. 3,397,986 | 0.05 |
| Compound R | comparison, U.S. Pat. No. 3,226,232 | 175.13 |
| Compound I-B | invention | 0.53 |
| Compound I-C | invention | 118.83 |
| Compound I-D | invention | 608.43 |
| Compound I-E | invention | 469.93 |
| Compound 1-H | invention | 40.03 |

The results in Table I show that the disulfides of this invention have good water solubility when compared to the prior art water-insoluble disulfide of U.S. Pat. No. 3,397,986 and the prior art water-soluble disulfide of U.S. Pat. No. 3,226,232. This would allow one skilled in the art to incorporate the disulfides of this invention into aqueous silver halide compositions without the need for organic solvents.

EXAMPLE 4

A low speed, 0.3-$\mu$m octahedral silver bromide emulsion (Emulsion A) was prepared in a conventional manner. This emulsion was split into two portions. Emulsion A1 is the control emulsion. The second portion (Emulsion A2) received 0.12 mg per Ag mol of the reduction sensitizer, thiourea dioxide, and was then heated at 60° C. for 20 minutes. Both portions then received common sulfur and gold sensitizers and were then heated at 70° C. for 40 minutes, followed by cooling to 40° C. The level of reduction sensitization in Emulsion A2 was chosen to obtain a high level of sensitivity and reduction-type fog. Separate aqueous solutions of bis(sodium p-glutaramidophenyl)disulfide (Compound I-E) and bis(2-amino-5-iodopyridinedihydroiodide)mercuric iodide (Compound E) were added to portions of Emulsion A2 at 40° C. Methanol solutions of bis(p-acetamidophenyl)disulfide (Compound D) were likewise added to portions of Emulsion A2. The liquid melts were held at 40° C. for 30 minutes prior to addition of extra ossein gelatin, water, Glycerin, and Saponin. The final melts were then mixed with bis(-vinylsulfonylmethyl)ether and immediately coated on cellulose acetate to give 300 mg silver per square foot and 400 mg gelatin per square foot. The resulting dried coatings were exposed for 0.1 second with 365 nm light through a stepped-density tablet and processed for 6 minutes in Kodak rapid x-ray developer. Levels of compounds added are in μmol per Ag mol. Speeds are measured at 0.3 density above D-min and are relative to Emulsion A1.

TABLE II

| | (Levels in $10^{-6}$ mol/Ag mol) | | | | |
|---|---|---|---|---|---|
| Emulsion | Compound D | Compound E | Compound I-E | Fog | Relative Speed |
| A1 | 0 | 0 | 0 | 0.122 | 100 |
| A2 | 0 | 0 | 0 | 0.381 | 316 |
| | 1.0 | 0 | 0 | 0.232 | 219 |
| | 10.0 | 0 | 0 | 0.114 | 148 |
| | 100.0 | 0 | 0 | 0.147 | 170 |
| | 0 | 0.005 | 0 | 0.415 | 347 |
| | 0 | 0.05 | 0 | 0.251 | 234 |
| | 0 | 0.5 | 0 | 0.085 | 62 |
| | 0 | 0 | 1.0 | 0.251 | 309 |
| | 0 | 0 | 10.0 | 0.186 | 191 |
| | 0 | 0 | 100.0 | 0.177 | 214 |

The results in Table II show that the water-insoluble disulfide, Compound D, of U.S. Pat. No. 3,397,986 can effectively reverse the reduction type fog of Emulsion A2 without adversely affecting the sensitivity of the control Emulsion A1. The mercuric salt, Compound E, also reverses the fog but causes a severe sensitivity loss. The disulfide compound of this invention, Compound I-E, is similar in activity to Compound D, does not require organic solvent for incorporation into the liquid emulsion, can be used effectively in combination with reduction-sensitized emulsions to give high sensitivity and low fog, and can be used as an environmentally safe substitute for mercury compounds.

EXAMPLE 5

A 0.56-μm X 0.083-μm 4% iodide, silver bromoiodide tabular emulsion (Emulsion B) was sensitized with 0,185 g sodium thiocyanate/Ag mol, 6.6 mg sodium aurous dithiosulfate dihydrate/Ag mol, 6.2 mg sodium thiosulfate pentahydrate/Ag mol, 0.88 g Compound M/Ag mol, and 0.088 g Compound N/Ag mol by holding at 61° C. for 15 minutes. The resulting sensitized emulsion was mixed with additional water, gelatin, and 1.75 g Compound P/Ag mol in preparation for coating. A secondary melt composed of gelatin, Compound O, and coating surfactants was mixed in equal volumes with the emulsion melt immediately before coating on a cellulose acetate support. This emulsion layer was then protected by a gelatin overcoat and hardened.

The resulting dried coatings, containing 75 mg silver per square foot, 220 mg gelatin per square foot, and 144 mg of Compound O per square foot, were exposed for 0.02 s through a stepped density tablet and 0.3 density Inconel and Kodak Wratten 23A filters with 5500K light. Exposed strips were then developed in either E-6 color reversal developer to form positive color images from which speed at 0.3 below D-max (maximum density) was obtained; or a negative-working developer using a variation of the E-6 process (rehalo) to form negative color images from which fog was obtained. To obtain a negative dye image from the E-6 process, the remaining unexposed silver halide following non-chromogenic development is dissolved out of the element. The developed silver remaining in the element is converted back to silver halide (commonly referred to as rehalogenation). Color development and the remaining steps in the E-6 process are completed to give a negative dye image. This rehalogenation version of the E-6 process, called E-6 Rehalo process, is useful for determination of fog in a photographic silver halide element.

Emulsion B1 was sensitized similarly to Emulsion B but bis(p-acetamidophenyl)disulfide (Compound D) was added at 0.01 mmol/Ag mol immediately before sensitizers. Emulsion B2 was sensitized similarly to Emulsion B but Compound D was added at 0.1 mmol/Ag mol. Emulsion B3 was sensitized similarly to Emulsion B but bis(sodium p-glutaramidophenyl)disulfide (Compound I-E) was added at 0.01 mmol/Ag mol. Emulsion B4 was sensitized similarly to Emulsion B but Compound I-E was added at 0.1 mmol/Ag mol. Low fog and high D-max are desirable. Speeds are relative to those of Emulsion B.

TABLE III

| | (Levels in mmol/Ag mol) | | | | |
|---|---|---|---|---|---|
| Emulsion | Compound D | Compound I-E | Fog | Relative Speed | D-max |
| B (control) | — | — | 0.529 | 100 | 2.29 |
| B1 (comparison) | 0.01 | — | 0.299 | 105 | 2.56 |
| B2 (comparison) | 0.1 | — | 0.066 | 38 | 2.79 |
| B3 (invention) | — | 0.01 | 0.445 | 85 | 2.41 |
| B4 (invention) | — | 0.1 | 0.075 | 58 | 2.72 |

These results show that the use of the water-soluble disulfide of this invention (Compound I-E) during the sensitization yields similar reductions in fog compared to the water-insoluble disulfide (Compound D). Compound I-E can be used to obtain equivalent photographic response compared to Compound D by one skilled in the art by appropriate adjustment of sensitizer levels, sensitization conditions, and levels of Compound I-E.

EXAMPLE 6

A 0.61-μm X 0.1-μm 4% iodide, silver bromoiodide tabular emulsion (Emulsion C) was sensitized with the sulfur and gold compounds and dyes of Emulsion B of Example 5, and with 31 mg Compound S/Ag mol by holding at 63° C. for 15 minutes. The sensitized emulsion was then divided into portions and mixed with solutions of various disulfides. A secondary melt composed of gelatin, Compound O, and coating surfactants was mixed in equal volumes with the emulsion melt immediately before coating on a cellulose acetate support. This emulsion layer was then protected by a gelatin overcoat and hardened. The resulting dried coatings, containing 75 mg silver per square foot, 220 mg gelatin per square foot, and 144 mg Compound O per square foot, were exposed for 0.02 s through a stepped density tablet and 0.3 density Inconel and Kodak Wratten 23A filters with 5500K light. Exposed strips were then developed in either E-6 color reversal developer to form positive color images from which speed at 0.3 below D-max (maximum density) was obtained; or a negative-working developer using a variation of the E-6 process (rehalo) to form negative color images from which fog was obtained. Low fog and high D-max are desirable. Speeds are relative to those of the control emulsion not containing disulfide.

TABLE IV

| Compound | Level mmol/Ag mol | D-min | Relative Speed | D-max |
|---|---|---|---|---|
| Control (comparison) | | 0.664 | 100 | 2.37 |
| Compound D (comparison) | 0.15 | 0.464 | 87 | 2.59 |
| | 0.3 | 0.245 | 107 | 2.77 |
| | 0.6 | 0.261 | 105 | 2.73 |
| Compound Q (comparison) | 0.6 | 0.614 | 126 | 2.4 |
| Compound R (comparison) | 0.6 | 0.719 | 105 | 2.25 |
| Compound I-E (invention) | 0.15 | 0.347 | 19 | 2.72 |
| | 0.3 | 0.214 | 12 | 2.76 |
| | 0.6 | 0.164 | 11.5 | 2.81 |
| Compound I-H (invention) | 0.15 | 0.406 | 16.5 | 2.56 |
| | 0.3 | 0.357 | 17.5 | 2.63 |
| | 0.6 | 0.256 | 41 | 2.65 |
| Compound I-C (invention) | 0.15 | 0.283 | 14 | 2.66 |
| | 0.3 | 0.218 | 16 | 2.77 |
| | 0.6 | 0.137 | 58 | 2.89 |
| Compound I-D (invention) | 0.15 | 0.426 | 145 | 2.54 |
| | 0.3 | 0.383 | 39 | 2.66 |
| | 0.6 | 0.328 | 69 | 2.7 |
| Compound I-B (invention) | 0.15 | 0.516 | 148 | 2.48 |
| | 0.3 | 0.432 | 141 | 2.56 |
| | 0.6 | 0.365 | 129 | 2.61 |
| Compound I-A (invention) | 0.15 | 0.45 | 145 | 2.6 |
| | 0.3 | 0.315 | 129 | 2.7 |
| | 0.6 | 0.172 | 60 | 2.86 |

The results in Table IV show that the water-soluble disulfides of this invention surprisingly give greater photographic activity than either the water-soluble 5-thioctic acid (Compound Q) of U.S. Pat. No. 2,948,614 or the water-soluble o-carboxyphenyl disulfide (Compound R) of U.S. Pat. No. 3,226,232. The disulfides of this invention also give low D-min and high D-max when compared to the water-insoluble disulfide (Compound D) of U.S. Pat. No. 3,397,986. Although relative sensitivities of the disulfides of this invention are low in this silver bromoiodide composition, one skilled in the art can reverse this sensitivity loss by utilizing materials such as the azaindenes as taught in U.S. Pat. No. 3,859,100.

EXAMPLE 7

A silver chloride photographic emulsion was precipitated by a double jet technique with the use of 1,8-dithiaoctanediol as a growth ripener. The resulting cubic emulsion had an edge length of 0.75 $\mu$m. Chemical sensitization was effected with one of the water-insoluble gold compounds of U.S. Pat. No. 2,642,361 in the presence of a cyanine yellow sensitizing dye, 1-(3-acetamidophenyl)-5-mercaptotetrazole, and potassium bromide. This sensitized emulsion is the control emulsion, Emulsion D. Sodium chloride was added to all emulsions before coating. Immediately prior to coating, the emulsions were co-mixed with a yellow image coupler dispersion which was stabilized with benzenesulfonic acid.

The co-mixture of Emulsion D and coupler dispersion was designated Part 1. In another case, mercuric chloride (Compound J) was introduced into the coupler dispersion and, after co-mixing with Emulsion D, was designated Part 2. To two separate portions of Emulsion D were added methanol solutions of bis(p-acetamidophenyl)disulfide (Compound D), these were then co-mixed with coupler dispersion and designated Part 3 and Part 4. To two more separate portions of Emulsion D were added water solutions of bis(p-glutaramidophenyl)disulfide (Compound I-E), these were then co-mixed with coupler dispersion and designated Part 5 and Part 6. Concentrations of Compounds D and I-E in Table V are in mmol per Ag mol.

All liquid silver chloride mixtures were coated on resin coated paper support to give 26 mg silver, 100 mg yellow coupler, and 77 mg gelatin per square foot. Dried coatings were subjected to a sensitometric gradation exposure of 0.1 s through a set of Kodak filters. The rapid access RA-4 process was used as described in Research Disclosure, Vol. 308, p. 933, 1989. Relative speeds are measured at 1.0 density. Low Δ Speed and Δ Fog after storage and low Δ Speed at different exposure temperatures are highly desirable.

TABLE V

| Experiment | Compound mmol/Ag mol | | | Fresh | | Incubation* | | HS** |
|---|---|---|---|---|---|---|---|---|
| | D | J | I-E | Relative Speed | Fog | Δ Speed | Δ Fog | Δ Speed |
| Part 1 (control) | 0 | 0 | 0 | 100 | 0.06 | +18.5 | +0.095 | +4.7 |
| Part 2 (comparison) | 0 | 0.0045 | 0 | 100 | 0.06 | +11.0 | +0.065 | +4.8 |
| Part 3 (comparison) | 2 | 0 | 0 | 91 | 0.06 | +17.0 | +0.075 | +1.8 |
| Part 4 (comparison) | 6 | 0 | 0 | 82 | 0.06 | +14.5 | +0.075 | +1.0 |
| Part 5 (invention) | 0 | 0 | 2 | 100 | 0.06 | +17.0 | +0.070 | +3.5 |
| Part 6 (invention) | 0 | 0 | 6 | 85 | 0.05 | +14.0 | +0.065 | +0.5 |

*2 week/120° F./50% Relative Humidity vs 0° F. control.
**Relative difference between exposures at 25 and 40° C.

These results show that the comparison water-insoluble disulfide (Compound D) is effective at stabilizing speed and fog after incubation relative to the control, and that it reduces the speed difference between exposure temperatures better than mercuric chloride. Compound I-E, the object of this invention, stabilizes speed and fog after incubation better than Compound D, while causing much less sensitivity loss, and also reduces the speed difference between exposure temperatures better than Compound D or mercuric chloride.

The other water-soluble disulfides of this invention showed similar activity in additional tests with this emulsion composition. This provides a method to stabilize high chloride silver halide emulsions without the use of hazardous and undesirable methanol, and provides an environmentally better alternative to mercury-containing stabilizers.

EXAMPLE 8

To a reaction vessel fitted with a motor-driven mixer were added 0.44 mol of a cubic AgBr emulsion with a grain edge-length of 0.71 μm and 5 g of gelatin. Distilled water was then added to reach a final weight of 450 g. The solution conditions of this liquid emulsion were subsequently adjusted to 60° C., pH 6.0, and pAg 6.5. To this liquid emulsion was slowly added 0.585 g of bis(sodium p-glutaramidophenyl) disulfide. No significant changes in solution conditions were observed. Controlled double-jet precipitation proceeded with thorough mixing and with 2.5M NaBr and 2.5M $AgNO_3$ solutions. The flow rates were linearly accelerated from 0.5 cc/min to 1.5 cc/min. The solution conditions were kept at 60° C, pH 6.0, and pAg 6.5 throughout the precipitation. A total of 0.12 mol of $AgNO_3$ and NaBr was each injected during the precipitation process. Emulsion samples were taken from the liquid emulsion during the precipitation for examination with Scanning Electron Microscope. Using Scanning Electron Microscope, we observed that during the precipitation, (110) crystal faces formed at the locations of the edges of the originally cubic emulsion grains. At the end of the precipitation, unsmooth and terraced structures formed on the emulsion surfaces.

EXAMPLE 9

Soluble disulfide compound used in precipitation of AgClI (111) tabular emulsion A 2-mole batch of a AgClI (111) tabular emulsion, containing 0.5 mole % iodide based on silver, was precipitated according to the method of Maskasky (U.S. Pat. No. 5,178,997 issued Jan. 12, 1993). The resulting tabular emulsions had an average aspect ratio of 17.5. The following emulsions were prepared.

Emulsion F1 was precipitated without any foggant added.
Emulsion F2: 60 mg of Compound I-D was added to the salt solutions.
Emulsion F3: 60 mg Compound I-D was added to the kettle prior to the start of the precipitation.
Emulsion F4: 60 mg Compound I-D was added to the silver nitrate solution.
Emulsion F5: 0.6 micromole $HgCl_2$ was added to silver nitrate solution.

All of the emulsion examples were sensitized by adding a spectral sensitizing dye, lowering the pH to desorb the growth modifier, adding a phthallated gelatin and adjusting the pH to coagulate the emulsion. The salts and growth modifier were removed by washing as described in U.S. Pat. No. 5,221,602 issued Jun. 22, 1993. Further sensitization was achieved by adding NaSCN, the salt of a benzothiazolium compound, a sulfur sensitizer and a gold sensitizer. The emulsions were heated to 60° C. for 20 minutes and after cooling 1-(3-acetamidophenyl)-5-mercaptotetrazole was added. The emulsions were coated with a color image dye-forming coupler on a support. Samples of the coatings were held for one week under each of two conditions (0 F to represent a fresh coating and 120 F to simulate the effect of unexposed film natural age keeping), exposed together on a Kodak 1B sensitometer for 1/25 second and processed together in Process C-41, a standard negative film process. Speed was calculated as negative log [exposure required to produce 0.15 density above minimum density]. The results are shown in Table VI below.

TABLE VI

| Emulsion | Disulfide In Precipitation | Soluble Disulfide In Precipitation | | | |
|---|---|---|---|---|---|
| | | Disulfide In Sensitization | D-min/0.15 spd 1 week 0 F. | 1 week 120 F. 50% RH | |
| F1 | — | — | 0.40/246 | 0.79/254 | comparison |
| F2 | salt | — | 0.19/248 | 0.47/254 | invention |
| F3 | kettle | — | 0.28/247 | 0.63/254 | invention |
| F4 | silver | — | 0.48/251 | 0.67/252 | invention |
| F5 | (Hg) | — | 0.09/248 | 0.18/260 | comparison |

EXAMPLE 10

Soluble disulfide compound used in sensitization of AgClI (111) tabular emulsion The soluble disulfide Compound I-D was also found to be a useful antifoggant when introduced into the sensitization process. In this example, Compound I-D was added to Emulsions F1 through F4 at 12 mg/mole Ag before the addition of the NaSCN. The emulsions were stored and processed as described in Example 9. The results are shown in Table VII below.

TABLE VII

| Emulsion | Disulfide In Precipitation | Soluble Disulfide In Sensitization | | | |
|---|---|---|---|---|---|
| | | Disulfide In Sensitization | D-min/0.15 spd 1 week 0 F. | 1 week 120 F. 50% RH | |
| F1 | — | — | 0.40/246 | 0.79/254 | comparison |
| F1S | — | 12 | 0.30/246 | 0.52/256 | invention |
| F2S | salt | 12 | 0.21/240 | 0.46/252 | invention |
| F3S | kettle | 12 | 0.26/254 | 0.59/256 | invention |
| F4S | silver | 12 | 0.49/250 | 0.68/251 | invention |

It can be seen from Tables VI and VII that Compound I-D is a useful antifoggant when introduced at various positions in the precipitation or sensitization of AgClI (111) tabular emulsions. The compound also stabilizes the emulsion coating to reduce the growth of fog upon keeping. Meanwhile the speed is hardly affected.

EXAMPLE 11

A silver chloride (100) tabular grain emulsion was precipitated as follows. A double jet precipitation of AgNO3 and NaCl was used for fast nucleation in the presence of small amounts of iodide followed by a large dilution addition of water containing the water soluble disulfide, Compound I-E. Then double jet addition of AgNO3 and NaCl was continued. The resultant emulsions, G1 to G4, were characterized by equivalent circular diameter (ECD) and the thickness was measured by a coated reflectance test (CRT):

| Emulsion | Compound I-E μmole/Ag mole | ECD/CRT μm/μm |
|---|---|---|
| G1 | 0 | 0.91/0.11 |
| G2 | 1 | 0.85/0.13 |
| G3 | 10 | 0.92/0.13 |
| G4 | 100 | 0.89/0.13 |

A magenta sensitizing dye was added to these emulsions followed by the addition of gold sulfide, heat digestion at 60° C. for 45 minutes, the addition of 1-(3-acetamidophenyl)-5-mercaptotetrazole, and the addition of potassium bromide. Immediately prior to coating, the emulsions were dual mixed with a magenta coupler dispersion and then coated on a paper support at 26 mg silver per square foot. They were subsequently subjected to sensitometric gradation exposure through a set of Kodak filters. The samples were processed with Process RA-4, a standard paper process, and the speed was measured at 1.0 absolute density. The results are shown in Table VIII.

TABLE VIII

| Emulsion | Soluble disulfide in make | | | |
|---|---|---|---|---|
| | Dmin | Toe | Speed | Contrast |
| G1 | 0.20 | 0.53 | 136 | 1.57 |
| G2 | 0.16 | 0.49 | 156 | 1.68 |
| G3 | 0.13 | 0.48 | 158 | 1.72 |
| G4 | 0.13 | 0.50 | 159 | 1.66 |

EXAMPLE 12

Emulsions G1 and G3 were sensitized as described in Example 11, except that temperature was 70° C., a tenfold amount of gold sulfide was used and a specified amount of Compound I-E was added prior to the dye, as described in Table IX. The emulsions were processed as described in Example 11. The results are shown in Table IX.

TABLE IX

| Emulsion | Soluble disulfide in make/finish | | | | |
|---|---|---|---|---|---|
| | Compound I-E Make/Finish μmole/Ag mole | Dmin | Toe | Speed | Contrast |
| G-1 | 0   0 | 0.18 | 0.49 | 158 | 1.69 |
| G-1 | 0   5 | 0.16 | 0.47 | 166 | 1.76 |
| G-1 | 0   15 | 0.14 | 0.38 | 154 | 2.05 |
| G-3 | 10   0 | 0.16 | 0.47 | 182 | 1.77 |
| G-3 | 10   5 | 0.14 | 0.43 | 180 | 1.90 |
| G-3 | 10   15 | 0.13 | 0.41 | 180 | 1.95 |

The results shown in Tables VIII and IX clearly show the fog reduction obtained by the addition of the soluble disulfide Compound I-E to the emulsion during precipitation and finish.

While the invention has been described in detail and with reference to specific embodiments thereof, it will be apparent to one skilled in the art that various changes and modifications can be made therein without departing from the spirit and scope thereof.

What is claimed is:

1. A silver halide photographic element comprising a silver halide emulsion in reactive association with a disulfide compound represented by the following formula:

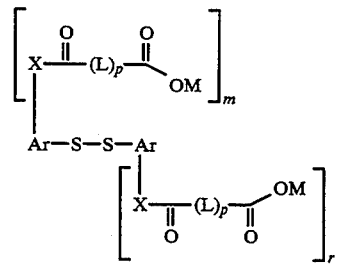

wherein

X is independently —O—, —NH— or —NR—, where R is an alkyl group, a fluoroalkyl group, an aryl group or a sulfonyl group;

m and r are independently 0, 1 or 2, with the proviso that m and r are not both 0;

M is —H or a cationic species;

Ar is an aromatic group; and

L is a linking group, where p is 0 or 1.

2. The photographic element of claim 1 wherein m and r are 1; Ar is an aromatic group having 6 to 10 carbon atoms; p is 1; and L is —(CH2)n—, where n is zero to 11.

3. The photographic element of claim 2 wherein Ar is an aromatic ring having 6 carbon atoms; L is —(CH2)n—, where n is 1 to 3; and M is —H— or an alkali metal cation.

4. The photographic element of claim 3 wherein X is —NH—.

5. The photographic element of claim 1 wherein the silver halide emulsion is greater than 50 mole % silver chloride.

6. The photographic element of claim 1 wherein the silver halide emulsion is greater than 95 mole % silver chloride.

7. The photographic element of claim 3 wherein the silver halide emulsion is greater than 50 mole % silver chloride.

8. The photographic element of claim 3 wherein the silver halide emulsion is greater than 95 mole % silver chloride.

9. A silver halide photographic element comprising a silver halide emulsion and a compound represented by the following formula:

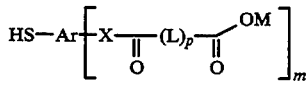

wherein

X is independently —O—, —NH— or —NR—, where R is an alkyl group, a fluoroalkyl group, an aryl group or a sulfonyl group;

m is 1 or 2;

M is —H— or a cationic species;

Ar is an aromatic group; and

L is a linking group, where p is 0 or 1.

10. The photographic element of claim 9 wherein m is 1; Ar is an aromatic group having 6 and 10 carbon atoms; p is 1; and L is —(CH$_2$)$_n$—, where n is zero to 11.

11. The photographic element of claim 10 wherein Ar is an aromatic ring having 6 carbon atoms; L is —(CH$_2$)$_n$—, where n is 1 to 3; and M is —H— or an alkali metal cation.

12. The photographic element of claim 11 wherein X is —NH—.

13. The photographic element of claim 9 wherein the silver halide emulsion is greater than 50 mole % silver chloride.

14. The photographic element of claim 9 wherein the silver halide emulsion is greater than 95 mole % silver chloride.

15. The photographic element of claim 11 wherein the silver halide emulsion is greater than 50 mole % silver chloride.

16. The photographic element of claim 11 wherein the silver halide emulsion is greater than 95 mole % silver chloride.

17. A silver halide photographic element comprising a silver halide emulsion in reactive association with a disulfide compound represented by the following formula:

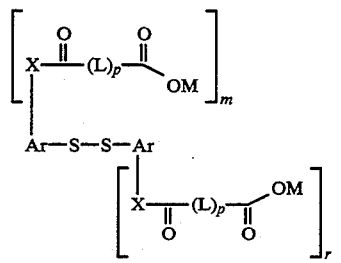

wherein

X is independently —O—, —NH— or —NR—, where R is an alkyl group, a fluoroalkyl group, an aryl group or a sulfonyl group;

m and r are 1;

M is —H or a cationic species;

Ar is an aromatic group; and

L is a linking group, where p is 0 or 1.

* * * * *